United States Patent [19]

Ford et al.

[11] Patent Number: 4,794,075

[45] Date of Patent: Dec. 27, 1988

[54] METHOD FOR LOCATING AND PURIFYING DNA CONTAINING SINGLE BASE MISMATCHES

[75] Inventors: John P. Ford, Tappan; David F. Novack, White Plains; Nancy J. Casna, Hopewell Junction, all of N.Y.

[73] Assignee: Lifecodes Corporation, Valhalla, N.Y.

[21] Appl. No.: 770,841

[22] Filed: Aug. 29, 1985

[51] Int. Cl.$^4$ .................... C12Q 1/68; G01N 33/48
[52] U.S. Cl. .......................... 435/6; 435/7; 435/803; 436/63; 436/501; 514/44; 536/27; 935/6; 935/9; 935/19; 935/23; 935/78; 935/81
[58] Field of Search ............... 435/6, 7, 803; 436/501, 436/63; 514/44; 536/27; 935/6, 9, 19, 23, 78, 81

[56] References Cited

PUBLICATIONS

Hale, P. et al., "Carbodiimide Inactivation of *Escherichia Coli* . . . ", *J. Biol. Chem.* 258 (12), 7828–7839 (Jun. 25, 1983).
*Proc. Nat'l Acad. Sci. USA* 72: 989–993 (1975) T. E. Shenk, et al., "Biochemical Method for Mapping Mutational Alterations in DNA with S1 Nuclease: The Location of Deletions and Temperature-Sensitive Mutations in Simian Virus 40".
*Biochemistry* 15: 4457–63 (1976) D. Kowalski, et al., "Mung Bean Nuclease I. Physical, Chemical, and Catalytic Properties".
*Proc. Nat'l Acad. Sci. USA* 80: 1579–83 (1983) S. G. Fischer and L. S. Lerman, "DNA Fragments Differing by Single Base-Pair Substitutions Are Separated in Denaturing Gradient Gels: Correspondence with Melting Theory".
*Nucl. Acid. Res.* 9: 3647–56 (1981) R. B. Wallace, et al., "Oligo Nucleotide Directed Mutagenesis of the Human $\beta$-Globin Gene: A General Method for Producing Specific Point Mutations in Cloned DNA".
*J. Virol.* 18: 205–210 (1976) J. Lebowitz, et al., "Chemical Modification of Simian Virus 40 DNA by Reaction with a Water-Soluble Carbodiimide".
*Nucl. Acid. Res.* 4: 1695–1711 (1977) J. Lebowitz et al., "Carbodiimide Modification of Superhelical PM2 DNA: Considerations Regarding Reaction at Unpaired Bases and the Unwinding of Superhelical DNA with Chemical Probes".
*Nucl. Acid Res.* 8: 4521–34 (1980) J. M. Kelly and B. E. H. Maden, "Chemical Modification Studies and The Secondary Structure of HeLa Cell 5.8S rRNA".
*Biochemistry* 6: 3632–39 (1967) N. W. Y. Ho and P. T. Gilham, "The Reversible Chemical Modification of Uracil, Thymine, and Guanine Nucleotides and the Modification of the Action of Ribonuclease on Ribonucleic Acid".
*Proc. Nat'l Acad. Sci. USA* 78(11): 6613–17 (1981) S. V. Suggs, et al. "Use of Synthetic Oligonucleotides as Hybridization Probes: Isolation of Cloned cDNA Sequences for Human $\beta_2$-Microglobulin".
*Proc. Nat'l Acad. Sci.* USA 80(1): 278–82 (1983) B. J. Conner, et al., "Detection of Sickle Cell $\beta^5$-Globin Allele by Hybridization with Synthetic Oligonucleotides".

(List continued on next page.)

*Primary Examiner*—Robert J. Warden
*Assistant Examiner*—Richard Wagner
*Attorney, Agent, or Firm*—Pennie & Edmonds

[57] ABSTRACT

A method for distinguishing fragments of DNA which contain single base mismatches from their perfectly paired homologues is disclosed. Single stranded regions within a duplex fragment are modified with carbodiimide, which reacts with unpaired guanine (G) and thymine (T) residues in DNA. Linear duplex DNA molecules do not react, while DNA molecules with single base mismatches react quantitatively with carbodiimide. Following reaction with carbodiimide, the DNA molecules are fractionated on high percentage polyacrylamide gels such that modified and unmodified fragments can be clearly distinguished. Application of this technique in order to located and purify DNA sequence differences responsible for phenotype variation and inherited disease is disclosed.

38 Claims, 13 Drawing Sheets

OTHER PUBLICATIONS

*Proc. Nat'l. Acad. Sci. USA* 80(7): 2007-11 (1983) D. H. Schulze, et al., "Comparison of the Cloned H-2K$^{bml}$ Variant Gene with the H-2K$^b$ Gene Shows a Cluster of Seven Nucleotide Differences".

*Biochemistry* 16(24): 5329-41 (1977) D. E. Kohne, et al., "Room Temperature Method for Increasing the Rate of DNA Reassociation by Many Thousandfold: The Phenol Emulsion Reassociation Technique".

*Biopolymers* 21: 665-677 (1982) R. Wieder and J. G. Wetmur, "Factors Affecting the Kinetics of DNA Reassociation in Phenol-Water Emulsion at High DNA Concentrations".

*J. Org. Chem.* 21: 439-441 (1956) J. C. Sheehan et al., "The Use of Water-Soluble and Basic Carbodiimides in Peptide Synthesis".

*J. Org. Chem.* 26: 2525-28 (1961) J. C. Sheehan, et al., "A Convenient Synthesis of Water-Soluble Carbodiimides".

*Gene* 26: 171-179 (1983) W. A. M. Loenen and F. R. Blattner, "Lambda Charon Vectors (CH 32, 33, 34 and 35) Adapted for DNA Cloning in Recombination-Deficient Hosts".

*Nature* 302: 33-37 (1983) D. J. Capon, et al., "Complete Nucleotide Sequences of the T24 Human Bladder Carcinoma Oncogene and its Normal Homoloque".

*Proc. Nat'l Acad. Sci. USA* 81: 4008-12 (1984) O. Fasano, et al., "Analysis of the Transforming Potential of the Human H-ras Gene by Random Mutagenesis".

*Proc. Nat'l Acad. Sci. USA* 74: 5463-67 (1977) F. Sanger, et al., "DNA Sequencing with Chain-Terminating Inhibitors".

*Anal. Biochem.* 114: 193-197 (1981) D. S. Holmes and M. Quigley, "A Rapid Boiling Method for the Preparation of Bacterial Plasmids".

*J. Mol. Biol.* 19: 548-555 (1966) F. H. C. Crick, "Codon-Anticodon Pairing: The Wobble Hypothesis".

*J. Biol. Struct. and Dynamics* 1: 509-521 (1983) P. Lu, et al., "Possible Molecular Detent in the DNA Structure at Regulatory Sequences".

*Nature* 304: 230-34 (1983) V. J. Kidd, et al., "$\alpha_1$-Antitrypsin Deficiency Detection by Direct Analysis of the Mutation in the Gene".

□ MALE
○ FEMALE
(DARKENED SYMBOLS SIGNIFY CANCER AFFECTED INDIVIDUALS)

STRATEGY 1

A $\underset{CH_3}{\overset{CH_3}{|}} \underset{CH_3}{\overset{CH_3}{|}} \underset{CH_3}{\overset{CH_3}{|}}$ (HYPOTHETICAL PATTERN OF AlvI METHYLASE)

B $\underset{CH_3}{\overset{CH_3}{|}} \underset{CH_3}{\overset{CH_3}{|}}$ (HYPOTHETICAL PATTERN OF DAM METHYLASE)

A $\underset{}{\overset{CH_3 \; CH_3 \; CH_3}{| \; | \; |}}$
B $\underset{CH_3 \; CH_3}{| \; |}$ (HYPOTHETICAL PATTERN OF HETEROLOGOUS MOLECULE)

FIG. 2A

STRATEGY 2

<u>Bam</u> HI-GATC ─────────── A
A ─────────── CTAG-<u>Bam</u> HI

EcoRI -AATT ------------ B
B ------------ TTAA-<u>EcoRI</u>

<u>Bam</u> HI-GATC ─────────── A
B ------------ TTAA-<u>EcoRI</u>

METHOD FOR LOCATING AND PURIFYING DNA CONTAINING SINGLE BASE MISMATCHES

FIELD OF THE INVENTION

This invention relates to the field of molecular genetics. More specifically, the invention relates to the chemical modification of nucleic acids and the localization and purification of specific DNA sequences.

BACKGROUND OF THE INVENTION

Sequence comparison among short, homologous DNA molecules to reveal differences as slight as a single base pair substitution is an important step toward understanding the genetic basis for phenotypic variation and heritable disease.

When a DNA sequence from individual A differs from the DNA sequence of individual B by a single base pair substitution, one general approach to analyze such single base pair substitutions is to separate the strands from individuals A and B, mix and reanneal one strand from A and one strand B; because the sequences are identical except at the substituted site, complementary strands will reform the duplex DNA structure (since the strands are from two different individuals such a duplex is referred to herein as a heteroduplex). The heteroduplex will be a perfectly based paired DNA molecule except at the site of the base pair substitution. At this point a mismatch will occur. That is rather than the normal A-T, or G-C base pair, an A-C, A-G, T-C, T-G, A-A, G,G, T-T, C-C mispairing will be presented (see for example Page 11 infra). By detecting such an event one can better understand the nature of phenotypic variation and the heritable basis for certain diseases as well as providing a rational scheme for screening for such diseases.

Past efforts to detect mispaired bases include: (1) $S_1$ and mung bean nuclease cleavage at the mismatched bases in heteroduplex DNA molecules (Shenk, T. E., et al, *Proc. Nat'l. Acad. Sci. USA* 72:989-993 (1975) and Kowalski, D., et al, *Biochem* 15:4457 (1976)) (these enzymes, however, cleave single base mismatches with relatively poor efficiency); (2) Changes in electrophoretic mobility in denaturing gradient polyacrylamide gels (Fisher, S. G. and Lerman, L. S., *Proc. Nat'l. Acad. Sci. USA* 80:1579-83 (1983)) (unless modified, this technique is able to detect only a fraction of differences in DNA base sequence); (3) Differential hybridization with oligonucleotide probes that differ by a single base (Wallace, R. B. et al *Nucl. Acid Res* 9:3647-56 (1981)) (this procedure is useful only if prior sequence information is available).

This invention overcomes the deficiencies of the prior art attempts to resolve single base pair mismatches by specifically "tagging" mismatched regions and detecting same electrophoretically. The invention also provides a method for purifying specific gene segments.

BRIEF DESCRIPTION OF THE INVENTION

This invention provides a method for detecting duplex DNA containing single base mismatches comprising:

forming a duplex DNA molecule containing at least one single base mismatch;

reacting said mismatched duplex DNA with a carbodiimide;

identifying said reacted mismatch duplex DNA by detecting a difference in electrophoretic mobility of said DNA when compared to the mobility of perfectly matched duplex control DNA.

In a further embodiment this invention provides a method for purifying perfectly matched heteroduplex DNA comprising (a) forming a mixture of perfectly matched and imperfectly matched heteroduplex DNA (b) reacting the mixture with a carbodiimide to label the imperfectly matched heteroduplexes;

(c) separating the labelled imperfectly matched heteroduplex DNA from the unlabelled perfectly matched heteroduplex DNA.

DETAILED DESCRIPTION OF THE DRAWINGS

FIG. 1 illustrates a typical pedigree demonstrating the inheritance of a disease (cancer) as an autosomal dominant trait.

FIG. 2 illustrates various types of hybrids that form upon reassociation of mixture denatured DNA from two individuals and two strategies for their discrimination. In strategy 1 DNA from individual A is reacted with AluI methylase and DNA from individual B is reacted with Dam methylase. Only heteroduplex DNA (A/B) will be resistant to both AluI restriction enzyme and MboI restriction enzyme (sensitive to Dam methylase). The vector will be treated with both methylases. Only recombinants with A/B inserts that are resistant to digestion with both AluI and MboI will be able to form plaques. In strategy 2 the DNA from individual A will be ligated to linkers with BamH1 restriction enzyme ends and the DNA from individual B will be ligated to linkers with EcoR1 restriction enzyme. Heteroduplexed DNA (A/B) wil have one BamH1 end and one EcoR1 and will only form recombinant colonies in vectors containing an insertion site composed of one EcoRI and one BamHI region.

FIG. 3 illustrates the nucleotide sequence of 371 base pair Pst I fragment of the pT24 oncogene. T6 refers to the Pst I fragment inserted into the Pst I site of M13mp8 in the direction of transcription. T9 refers to the fragment inserted in the opposite orientation. The boxed sequences are differences between the oncogene and its non-transforming homologue pTPT. Thus, the boxed sequence at position 90 is not present in pTPT. Single base substitutions in the oncogene are shown at position 220 (oncogenic glycine to valine substitution) and position 266 (silent mutation in histidine codon). An axis of symmetry is also indicated.

FIG. 4 illustrates M13: H-ras Recombinants. The structures of the M13mp8 recombinants are shown. The heavy line represents the 371 base pair Pst I fragment from pT24 and the 365 base pair Pst I fragment from pTPT that was inserted into the M13mp8 polylinker. The solid arrow indicates the site of hybridization of the M13 pentadecamer primer that was used for primer extension. The wavy line shows the 5'-3' direction of primer extension. (See Materials and Methods for details). Oncogene recombinants are designated T6 and T9. In oncogene recombinant T6, the internal Sma I site of the 371 base pair Pst I fragment is closest to the Sma I site of the M13 polylinker. In oncogene recombinant T9, the Pst I fragment is inserted in the opposite orientation. Homologous wild type recombinants are designated P6 and P9. In wild type recombinant P6, the 365 base pair Pst I fragment is inserted in the same orientation as in T6. In wild type recombinant P9, the 365 base pair Pst I fragment is in the same orientation as T9.

FIG. 5 illustrates heteroduplex pairs formed by mismatch hybridization. Heteroduplex pair (A) was formed from the labelled strand of primer extended P6 and its complementary strand from unlabelled T6RF. Heteroduplex pair (B) was formed from the labelled strand of primer extended T9 and its complimentary strand from P9Rf. Heteroduplex pair (C) was formed from the labelled strand of T6 and its complementary strand from P6RF. Heteroduplex pair (D) was formed from the labelled strand of P9 and its complimentary strand from T9RF. The 6 base unpaired region and single base mismatches are indicated for each heteroduplex. Restriction enzyme sites used in the study are shown as well as restriction fragment lengths.

FIG. 6 illustrates the reaction of carbodiimide at restriction fragment ends.

A. Isolated 365 base pair Pst I fragment from primer extended P6 was treated as indicated and run on a 12% polyacrylamide gel. Lanes 1, 2 and 3) incubated at 30° C., 37° C., and 45° C. without carbodiimide. Lanes 4, 5 and 6) reacted with carbodiimide (as described in Materials & Methods) at 30° C., 37° C., and 45° C.

B. Isolated 228 base pair Sma I fragment from primer extended P9 was treated as indicated and run on a 12% polyacrylamide gel. Lanes 1, 2, 3 and 4) incubated at 30° C., 37° C., 45° C., and 55° C. without carbodiimide. Lanes 5, 6, 7 and 8) reacted with carbodiimide at 30° C., 37° C., 45° C., and 55° C.

FIG. 7 illustrates the effect of 6 base unpaired region on heteroduplex mobility. Primer extended P6 and heteroduplex A (FIG. 3) DNA were cleaved with Sma I, separated on a 5% gel and the 167 base pair band was purified as described in Materials and Methods. The purified DNA was then run on a 12% polyacrylamide gel. Lane (1) 167 base pair Sma I fragment from primer extended P6. Lane (2) denatured DNA from the 167 base pair Sma I fragment. Lane (3) 167 base pair Sma I fragment isolated from heteroduplex A (see FIG. 5). Heteroduplex A contains a six base unpaired region and shows a decreased mobility in the gel. The heteroduplex migrates at the same position as fragments of 650 base pairs. Double strand DNA molecular weight markers are indicated.

FIG. 8 illustrates the analysis of carbodiimide modification of six base unpaired region with the sequence GGGGCT on a 12% polyacrylamide gel. Lane (1) 167 base pair Sma I fragment from primer extended P6 purified as described in Materials and Methods. Lane (2) Sma I fragment after reaction with carbodiimide at 30° C. Lane (3) Sma I fragment from heteroduplex A (see FIG. 5) which has a six base unpaired region (GGGGCT). Lane (4) heteroduplex Sma I fragment reacted with carbodiimide at 30° C.

FIG. 9 illustrates the analysis of carbodiimide modification of six base unpaired region with the sequence CCCCGA on a 12% polyacrylamide gel. Lane (1) 167 base pair Sma I fragment from primer extended T6. Lane (2) Sma I fragment after reaction with carbodiimide at 30° C. Single stranded DNA present in lane 1 is quantitatively modified. Lane (3) Sma I restriction fragment from heteroduplex C (see FIG. 5) which has a six base unpaired region (CCCCGA). Lane (4) heteroduplex Sma I fragment reacted with carbodiimide at 30° C.

FIG. 10 illustrates the mobility shifts due to ccarbodiimide modification.

A. The 228 base pair Sma I fragment was reacted as indicated, cleaved with Sau III AI and the fragments were separated on a 15% polyacrylamide gel. Lane (1) unmodified homoduplex (primer extended P9); Lane (2) unmodified heteroduplex B (See FIG. 5). Lanes 3, 5 and (7) homoduplex reacted with carbodiimide at 30° C., 37° C., and 45° C., respectively. Lanes 4, 6 and (8) heteroduplex B reacted with carbodiimide at 30° C., 37° C. and 45° C., respectively.

B. The 365 base pair Pst I fragment was reacted as indicated, doubly digested with Sma I and Sau IIIA1 and the fragments were separated on a 15% polyacrylamide gel. Sau III AI did not digest to completion so different quantities of the 365 and 213 base pair partial digestion products are evident in the lanes. Fragment lengths are indicated to the left and mobility shifts caused by the presence of the 6 base unpaired region are shown by parenthesis. Lane (1) unmodified homoduplex (primer extended P6); Lane (2) unmodified heteroduplex A (see FIG. 5). Lanes 3, 5 and (7) homoduplex reacted with carbodiimide at 30° C., 37° C. and 45° C., respectively. Lanes 4, 6 and (8) heteroduplex B reacted with carbodiimide at 30° C., 37° C. and 45° C., respectively.

FIG. 11 presents diagrammatic illustrations of "tangles" which can be formed when a repeated DNA sequence hybridizes with its complement located elsewhere in the genome.

DETAILED DESCRIPTION OF THE INVENTION

Figure 1:
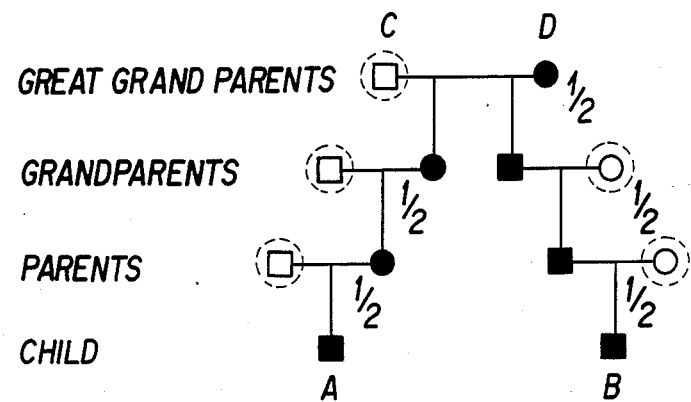

This invention provides a method for the detection and recovery of DNA sequences which contain single base mismatches by applying a "tag" following denaturation and reannealing of a restriction endonuclease digest of a mixture of the samples to be compared. The "tag" is specific for unpaired regions of DNA. Reassociation of single strands from identical fragments produce perfectly paired homoduplexes, whereas, reassociation of single strands from fragments which differ at a single base will generate heteroduplexes containing a mismatched pair. The "tag", when bound, alters the electrophoretic mobility of only the heteroduplex in a polyacrylamide gel and thus facilitates the detection and recovery of the fragment of interest.

The "tag" chosen is carbodiimide, since it modifies only unpaired guanine (G) and thymine (T) residues in supercoiled DNA without affecting perfect Watson-Crick pairs (Lebowitz, J., et al, *J. Virol* 18:205–210 (1976) and Lebowitz, J., et al, *Nucleic Acid Res.* 4:1695–1711 (1977)). At least one heteroduplex formed from the reassociation of any two molecules which differ by a single base pair will contain a mismatched G or T; thus all substitutions should be accessible as the specificity of carbodiimide is preserved in mismatched pairs in DNA.

This event is anticipated since Kelly & Maden (*Nucleic Acid Res.* 8:4521–34 (1980)) have shown, in examining the secondary structure of ribosomal RNA, that carbodiimide reacts with mispaired uracil (U) and G amid more stable pairs as it does with the same bases in unpaired stretches.

The ends of a blunt end DNA molecule are destabilized relative to interior portions and their availability to carbodiimide modification could obscure differences resulting from internal mismatches. However, Kelly & Maden (supra) also showed that while rG:rC pairs at the terminus of a double stranded region of rRNA were subject to modification by the base specific reagent bisulfite, they were unreactive to carbodiimide, suggesting further benefits of the choice of carbodiimide. Finally, carbodiimide modification is reversible by incubation under mild, slightly alkaline conditions (pH 10.5, 21° C.) which do not affect duplex DNA (Ho, N. W. Y, and Gilham, P. T., *Biochem.* 6:3632–39 (1967)).

In the Examples which follow, an assay involving electrophoresis in high percentage polyacrylamide gels of heteroduplexed DNA molecules with sequence alterations as small as a single base mismatch is described. Carbodiimide quantitatively modified the G and T bases in such mismatches resulting in a reduction in migration through the polyacrylamide gel.

The ability to selectively modify single base mismatches and then detect same has immedaate utility in several areas of molecular genetics. In a first embodiment this invention may be used as a system for mutation detection. This embodiment contemplates the use of an oligonucleotide probe (either isolated from a natural source or chemically synthesized) which may be labelled with an analytically detectable reagent. DNA sequences in a sample are then tested employing the method of the subject invention to identify any sequences differing from the probe sequence by at least one single base pair. Attempts to detect single base changes have relied upon mutations which altered restriction enzyme cleaning sites, however, since mutations which alter restriction sites eepresent only a small sub-set of the total mutation possible such a detection system is thus of only limited utility. As mentioned previously an alternative procedure involves the use of oligonucleotides which span the region in which the point mutation is to be detected. The length of the oligonucleotide is selected such that a single base mismatch results in a hybrid of decreased stability (see for example: Suggs, S. V. et al. *Proc. Nat'l Acad. Sci. USA* 78(11):6613–17(1981); Conner, B. J. et al., *Proc. Nat'l Acad Sci, USA* 80(1):278:82(278–82(1983); and Schultze, D. H. et al. *Proc. Nat'l Acad. Sci USA* 80(7):2007–11(1983). The limitations of such an approach include low sensitivity because of the constraint placed upon the hybridization conditions posed by the need to distinguish perfectly matched and single base mismatched DNAs; a substantial background hybridization because of the redundency inherent in the use of short length oligonucleotides, and the need for precisely controlled temperature of hybridization and elution in order to discriminate between a perfectly matched duplex DNA and a DNA duplex containing a single base mismatch.

The process of the subject invention permits the use of longer oligonucleotides thus substantially reducing the background hybridization problem experienced in the prior art. In addition by modifying the mismatch itself assay conditions may be employed that increase the sensitivity of detection.

In another embodiment the process of this invention provides a means for the purification of unique DNA sequences. The development of the procedure requires that there exist pedigrees which demonstrate the inheritance of the disease in a clear cut fashion. This situation exists for colon cancer, breast cancer, and cystic fibrosis. Such pedigrees exist for a variety of other diseases. FIG. 1 provides a hypothetical pedigree for colon cancer.

In the pedigree illustrated in FIG. 1, children A and B both inherited the gene which predisposes to colon cancer, and they inherited it from a common great grandparent.

Even though the DNA that A and B share in common includes the gene which predisposes to colon cancer that they inherit from their common great grandparent, the fraction of DNA that A and B share in common is a small fraction of their total DNA. With each generation half of the DNA contributed was from an unrelated male or female (symbols surrounded by dotted circles in FIG. 1). Thus if one were able to isolate the DNA that A and B inherit in common from C and D, one would be left (in the case of this illustration) with only 1/64×2 of the DNA but including the region which contains the gene, the mutant allele of which predisposes to colon cancer. By achieving the isolation of the DNA inherited in common, one has enriched 32 fold for the gene which predisposes to colon cancer.

The method of separating the DNA inherited in common away from the DNA not inherited in common takes advantage of the fact that about 1 out of 400 DNA bases is different between two individuals that are not related. Therefore, the DNA which is not inherited in common (not related) will have sequence differences about every 400 DNA bases. The DNA inherited in common will not have any (or very, very few) DNA base differences. See the illustrative examples below.

| inherited in common | not inherited in common |
|---|---|
| individual A | |
| A T G C T C G T A G G A G T C T | |
| T A C G A G C A T C C T C A G A | |
| individual B | |
| A T G C T C G T A T G A G T C T | |
| T A C G A G C A T A C T C A G A | |

It can be seen that the DNA regions not inherited in common have differences in their DNA sequence. When these DNA sequences are heated such that the two DNA strands come apart, mixed and are then allowed to cool such that the DNA strands reanneal, the following are among the structures will generated if the DNA from A pairs with the DNA from B.

| inherited in common | | | | | | | | non inherited in common | | | | | | | |
|---|---|---|---|---|---|---|---|---|---|---|---|---|---|---|---|
| (A) | A | T | G | C | T | C | G | T (I) | (A) | A | $^G$ | G | A | G | T | C | T (II) |
| (B) | T | A | C | G | A | G | C | A | (B) | T | $_A$ | C | T | C | A | G | A |

It can be seen that the mismatched base (G/A) results in the case where the DNA was not inherited in common.

The ultimate goal is then purifying structure I away from structure II. However, there are two technical hurdles which stand in the way of attempting such purification. These hurdles are: (A) reannealing DNA in complex human genome and (B) removing self annealed DNA.

Figure 11:
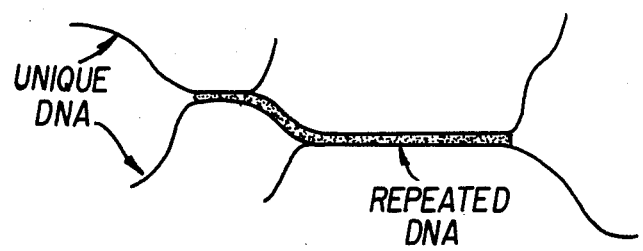

(A) If the DNAs from individual A and individual B are heated and then cooled they will base pair. However, the nature of the human genome (the entire DNA complement) is such that it includes repeated DNA sequences. That is, the same or nearly the same DNA sequence (say a 300 base pair stretch) occurs many times in the genome. While much of the DNA is unique (that is, if it occurs twice - 1 maternal and 1 paternal copy), some repeated DNA sequences are dispersed within these unique sequences. This situation has the potential for causing problems if the repeated DNA sequences from one region hybridize to the same repeated DNA sequences but in a different unique DNA context. Structures called "tangles" can be generated which can be visualized in the electron microscope as shown in FIG. 11.

By modifying a technique called PERT (phenol emulsion reassociation technique) as described by Kohne, D. E. et al. (*Biochemistry* 16 (24):5329–41 (1977)) and by Wieder, R. and J. G. Wetmur (*Biopolymers* 21:655–677 (1982)), the contents of each of which are incorporated herein by reference, human genomic DNA can be reannealed. This apparently results from the unique sequence in the proper context hybridizing and displacing the hybridizing repeated DNA sequences. As modified and improved the PERT technique performed in the presence of 5–10% formamide. DNA 20,000 base pairs long can be reannealed using this procedure.

(B) After DNA is heated (or treated with alkali) its two strands separate. The goal with respect to the present invention is to obtain those molecules of double stranded DNA which reform and consist of one strand derived from individual A and one strand from individual B (i.e. heteroduplex molecules). However, half the mass of double stranded DNA which is obtained will actually be composed of two strands of DNA from individual A or two strands from individual B (FIG. 2). These molecules must be removed.

Restriction enzymes cleave DNA at specific sequences. Restriction enzymes exist together with enzymes called methylases. A restriction enzyme has cognate methylase. The methylase protects the specific sequence from cleavage which is the normal target for its restriction enzyme. The selection of particular restriction enzyme/methylase combination is within the skill of the artisan in this field. For example, the DNA of individual A is treated with one methylase, say that AluI enzyme, and the DNA of individual B is treated with DAM methylase. These two enzymes are chosen because the four base recognition sequence of each enzyme occurs on average every 200–400 bases in the human genome. If the analysis is restricted to large molecules, after hybridization only AB DNA molecules will be resistant to both AluI and MboI (Dam restriction enzyme). Thus in a cloning system which requires relatively long pieces of DNA for successful integration, only AB DNA will provide such a substrate. (see below).

In an alternative system to insure that one strand of the duplex is contributed by the DNA of one individual (A) and the other strand is contributed by a second individual (B), DNA is isolated from individuals (A) and (B) of FIG. 1 and reduced to roughly "gene-size" pieces, this may be accomplished by endonuclease digestion or by physical means such as by shearing. If an endonuclease is employed it is preferred to use one which yields blunt-ended digestion products such as AluI, BalI, HaeIII, NruI, PvuII, SmaI and the like. If, however, an endonuclease which yields a single-strand overlapping region is used such reaction products should be converted to blunt-ended molecules by removal of the overlapping region such as by S1 nuclease digestion.

After digestion the blunt ends are end-labelled by the addition of a specific oligonucleotide linker. Thus the DNA fragment from individual (A) are end-labelled with an oligonucleotide sequence comprising the EcoRI restriction site whereas the DNA framments from individual (B) are end-labelled with an oligonucleotide sequence comprising the BamI restriction site. The DNA molecules are then introduced into cloning vectors adapted to accept DNA molecules possessing once EcoRI terminus andone Bam HI terminus. Molecules possessing homologous tails (e.g. 2 EcoRI or 2 Bam HI tails) could not be successfully ligated into such a vector.

After successfully providing a method for reannealing DNA in a complex human genome and removing self annealed DNA, it remains necessary to distinguish between perfectly matched DNA hybrids (FIG. 2D) and hybrids which contain single base mismatches (FIG. 2C) which have been integrated into the cloning vector. As described in detail below the DNA hybrids, prior to their integration into the cloning system, are reacted with carbodiimide, a reagent which preferentially labels mismatched DNA regions. Carbodiimides useful for practicing the instant invention are described in Sheenan, J. C. et al., *J. Org. Chem.* 21: 439 (1956) and Sheehan, J. C. et al. *J. Org. Chem.* 26: 2525 (1961). The selection of a particular carboodiimide is well within the skill of the artisan after consideration of the parameters of steric hinderence, water solubility and the like. 1-cyclohexyl-3-(2-morpholinoethyl) carbodiimide compounds were found to be particularly useful. Once integrated into the cloning vector, the C and D types can be further discriminated by employing a host in which the mismatched carbodiimide tagged segment cannot be repaired and thus replicated. A bacterial mutant defective in DNA repair such as UVR-A, recA mutants of *E. coli* are used. Thus the only colonies in which perfect matched segments are contained within the plasmid DNA will survive and grow. This procedure provides a method for the preferential recovery and enrichment of the perfectly matched duplexes among which is contained the genetic information of interest and which may be analyzed directly or subcloned.

Because in the PERT/methylase strategy discussed above long heteroduplex molecules are created (~20 kb), an alternative cloning methodology using the same bacterial strain (UVR A, RecA) is employed. The vector is λ phage derivative, λ Sep 6-lac5, as described by Meyorwitz, E., & D. Hogness (*Cell* 28: 165–176 (1982)) or Charon 35 as described by Loenen, WAM and F. R. Blattner (*Gene* 26: 171–179 (1983)). This is an EcoRI accepting vector with a 7-20 kb insert capacity. In this embodiment the self annealed DNA is removed by treating vector arms with both AluI and DAM methylase. The DNAs which are heteroduplexed are treated separately with methylases as described above. After the insert is ligated into the vector, the mixture is treated with AluI and MboI restriction enzymes. Only the heteroduplexed molecules will remain intact and form plaques.

In another embodiment, the carbodiimide-modified DNA is separated from the unmodified DNA by immunoadsorption, e.g., by passing the modified and unmodified DNA through a column packed with anti-carbodiimide antibody attached to a matrix. The unmodified DNA passes through but the carbodiimide-modified DNA is retained in the column.

In another embodiment the carbodiimide modified and unmodified DNA may be separated by a two dimensional gel electrophoresis procedure. According to this method the sample containing both modified and unmodified species are subjected to polyacrylamide gel electrophoresis in a first dimension. The carbodiimide moieties are then removed in situ by treating the gel with alkali (pH 10.5). The samples are then electrophoresed in a second dimension at right angles to the first dimension. DNA which does not alter its mobility is recovered for cloning.

Figure 12:
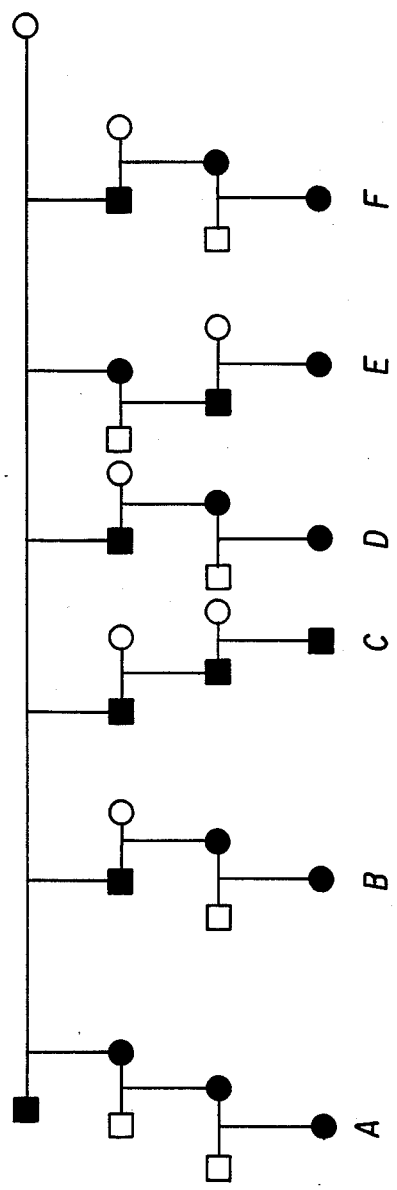
FIG. 12 illustrates a typical pedigree for a form of inherited breast cancer.

In a final embodiment the probes generated by the A/B comparison procedure can be used in a screening system to identify comparable regions in other family members. FIG. 12 represents a typical pedigree for an inherited form of breast cancer.

Figure 13:
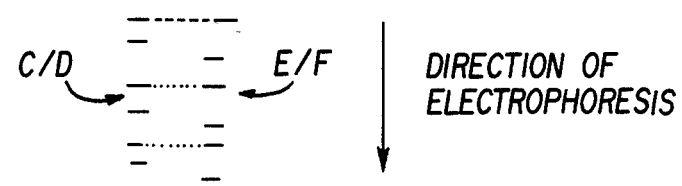
FIG. 13 illustrates the results of Southern blot analysis of various DNA fragments from individuals indentified in FIG. 12 according to the subject invention.

When the DNA comparison that was performed between A and B is now performed between C and D, and between E and F also, one generates three "libraries" of cloned DNA fragments. The DNA from such "libraries" so generated are immediately treated with restriction enzyme such that the population of human DNA inserts are cut out. This complex mixture is then subject to the Southern blotting procedure. Techniques exist to blank out the vector DNA (the plasmid or phage DNA) and also any repeated DNA sequences in the human DNA inserts. A typical results for Southern's of C against D DNA, and E against F DNA probed with nick-translated A against B DNA would appear as shown in FIG. 13. With reference to FIG. 13 it should be noted that the dotted lines which connect the bands which migrate at the same rate in the C/D and E/F comparisons. These represent sequences which occurred in A/B (source of radioactively labeled DNA probes) as well as in the C/D and E/F libraries. These sequences are very likely to be closely linked to the gene for inherited breast cancer. The libraries should contain only identical, co-herited DNA sequences of comparisons between the DNA of individuals A and B, or C and D, or E and F. The individual plaques corresponding to the bands can then be "fished" out of the library by conventional plaque assays.

General Methods and Materials

The following methods and materials used in connection with the Examples which follow.

Restriction enzymes were purchased from Bethesda Research laboratories or New England Biolabs and used as directed by the supplier. Radiochemicals were purchased from Amersham International. Acrylamide and Bisacrylamide were purchased from Bio-Rad. M13 pentadecamer primer and Klenow fragment of DNA polymerase I were purchased from Bethesda Research Laboratories. 1-cyclohexyl-3-(2-morpholinoethyl) carbodiimide metho-p-toluenesulfonate was purchased from Aldrich Chemical Co. Inc. and prepared as a 0.5M aqueous solution. pT24, a human H-ras oncogene containing plasmid (Capon, D. J. et al. *Nature* 302:33–37 (1983)) and pTPT, the wild type homologue containing plasmid (Fasano, O. et al., *Proc. Nat'l. Acad. Sci. USA* 81: 4008–12 (1984)) were obtained from Cold Spring Harbor Laboratories.

Construction of M13 Recombinants

Figure 3:
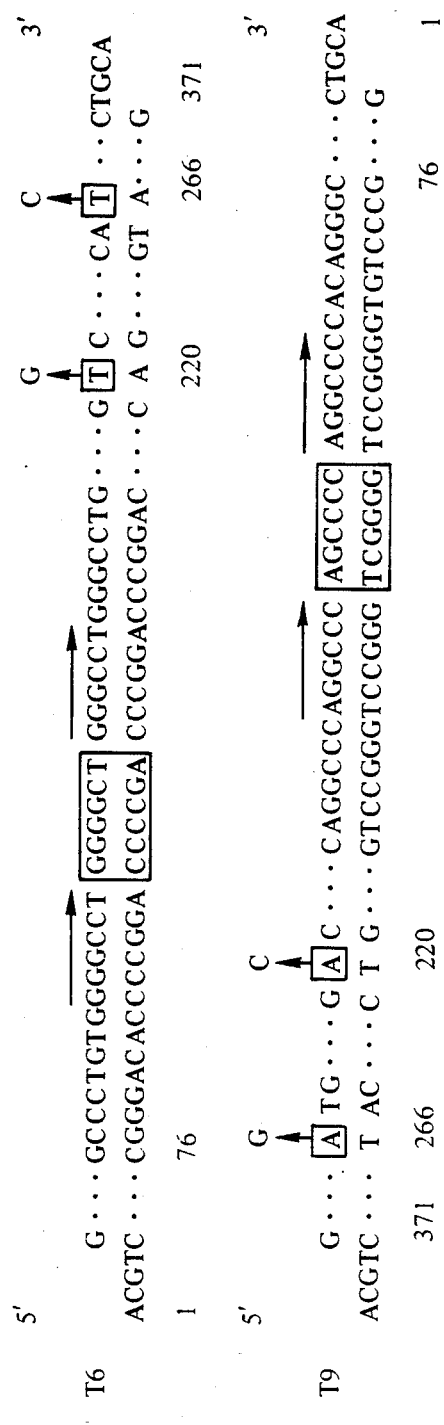

A Pst I fragment including the 5' noncoding region and the first exon from pT24 and pTPT were sequenced by interrupted synthesis (Sanger F, et al 74:5463–67 (1977)). A 371 base pair Pst I fragment of H-ras oncogene DNA and a 365 base pair Pst I fragment from homologous wild type DNA were isolated from pT24 and pTPT, respectively. These Pst I fragments are of different lengths due to a six base pair difference in pT24 (FIG. 3). Pst I fragments containing the 5' noncoding region were ligated (16 hours at 14° C. in 50 mN tris HCL (pH 7.6), 10 mM MgCl$_2$, 10 mM DTT, 1 mM ATP) into the Pst I site of M13mp8 (A cloning vector available from Bethesda Res. Lab. Inc. Gaitherburg, MD). Ligation reactions were done with 40 ng/ul of DNA using a 4 fold excess of insert to vector and 8 units/ul of T4 DNA ligase. *E. coli* strain JM103 was transformed with these ligated DNAs (Maniatis, T. et al Molecular Cloning: A Laboratory Manual Cold Spring Harbor (1982)) and plated on YT plates containing Xgal. DNA was prepared by a miniprep procedure (Holmes D. S. and M. Quigley *Anal Biochem* 114:193–97(1981)) from insert containing colonies. Recombinants contained the Pst I fragment inserted in both orientation (FIG. 4).

Primer Extensions

Figure 4:
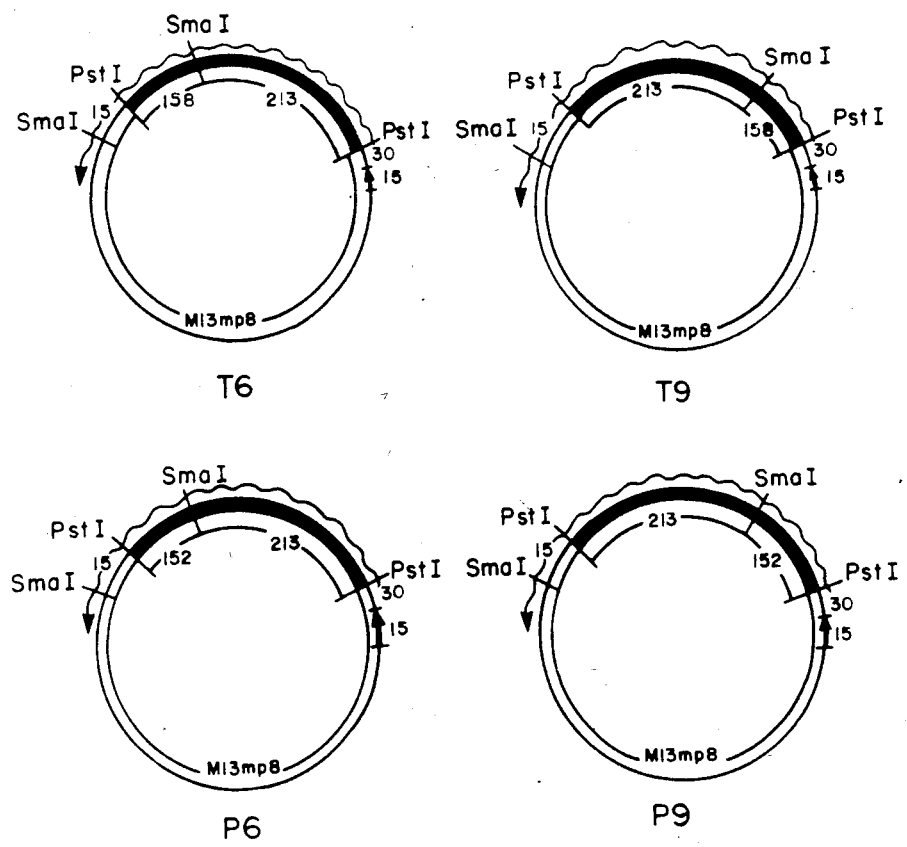

Single strand M13 phage DNA containing oncogene and wild type Pst I fragment was labelled with $^{32}$P-dATP by primer extension (FIG. 4). The reaction mixture consisted of 400 ng single strand phage DNA, 4 ng pentadecamer primer in 7.0 mM Tris-HCl (pH 7.5), 7.0 mM MgCl$_2$, 50.0 mM NaCl in 10 ul. The mixture was heated to 100° C. for 2 minutes and incubated at 42° C. for 1 hour. The reaction mixture was brought to 20 ul with 60 uCi $^{32}$P-dATP, 0.5 ul each of 10 mM dGTP, dCTP, dTTP, 2 ul 0.1M DTT and 5 units Klenow fragment and incubated at room temperature for one hour. The reaction was chased for 15 minutes with 0.5 ul 10 mM dATP and phenol extracted. This double stranded molecule (with one labelled strand) can be cleaved with restriction endonucleases.

Heteroduplex Formation

Figure 5:
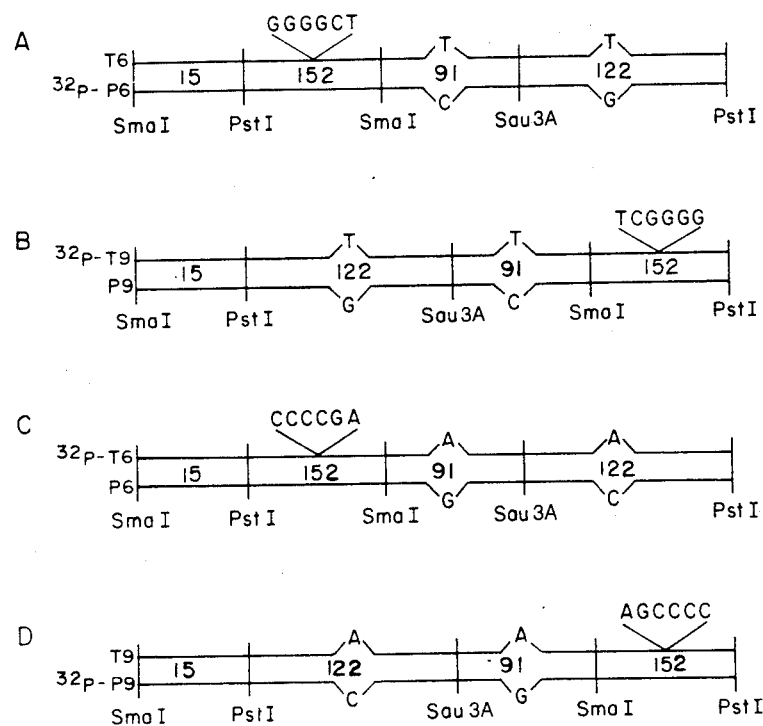

Primer extended M13 recombinants were digested with Pst I or Sma I. In the presence of 50 fold excess homologous, unlabelled M13 RF that had been similarly cleaved (final reaction volume 150 ul), the labelled restriction enzyme digests were heat denatured (100° C. for 15 minutes). Excess unlabelled DNA was added to favor heteroduplex formation. The fragments were hybridized at 42° C. for 60 minutes (FIG. 5). Homoduplex fragments from primer extended DNA were not denatured and renatured.

Fragment Purification

Polyacrylamide was prepared as a 30% stock solution (30:0.8, acrllamide:Bis). DNA fragments were run through a 5% polyacrylamide gel, 0.1M Tris-borate (pH 8.0), 1 mM EDTA, and visualized by autoradiography. Fragments were electroeluted from a gel strip in 0.05M Tris-borate buffer overnight at 2 V/cm. DNA was phenol extracted three times, chloroform extracted, precipitated in 0.35M ammonium acetate and washed with 70% ethanol.

Carbodiimide Reaction

DNA fragments were incubated with 0.1M carbodiimide, 0.1M sodium borate (pH 8.5) for 4 hours at varying temperatures. Samples were diluted 10 fold with water and precipitated twice in 0.25M ammonium acetaee. The precipitate was washed three times with 70% ethanol. DNA was cleaved as described in Example I to separate fragments containing mismatches.

Gel Electrophoresis

Separation of fragments after reaction with carbodiimide was achieved using 12%–15% polyacrylamide gels. Gels were run in a recirculating buffer of 40 mM Tris, 20 mM NaCl, 1 mM EDTA (pH 8.0) at 150 volts for 7–10 hours at 30° C. and autoradiographed.

EXAMPLE I

This example demonstrates the ability of the carbodiimide reaction used in conjunction with the subject invention to resolve single mismatches in duplex DNA.

A short region including the initial protein codin region of the H-ras oncogene serves as a model system to test the carbodiimide reaction with mismatched DNA. When this fragment is hybridized to non-transforming homologous DNA, the heteroduplexed molecule contains a six base unpaired region and two single base mismatches (FIG. 5). These mismatched structures within the DNA segments are potential sites for modification by carboiimide.

(A) Reaction of Carbodiimide at Fragment Ends

The effect of carbodiimide modification upon the migration of DNA segments in high percentage polyacrylamide gels was tested. Restriction enzyme digested DNA which was either perfectly double stranded (Sma I digest) or had protruding single stranded ends (Pst I digest) was reacted with carbodiimide prior to electrophoresis. Digestion with Pst I generates 3' overhangs with the sequence 5' TGCA 3'. T and G residues are potential sites of carbodiimide modification. Sma I produces blunt end fragments with three G-C pairs at the fragment end. Such fragments would be expected to be resistant to carbodiimide modification.

Figure 6A:
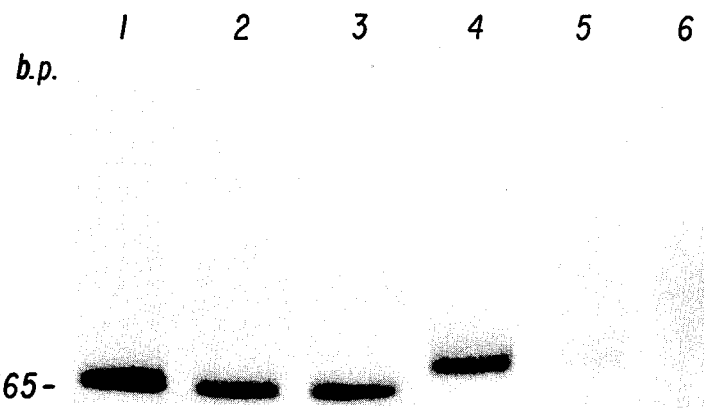

A 365 base pair Pst I fragment was isolated from primer extended P6 (FIG. 4). The purified fragment was reacted with carbodiimide at 30° C., 37° C., and 45° C. and analyzed by autoradiography following polyacrylamide gel electrophoresis (FIG. 6A). After carbodiimide modification at 30° C. the Pst I fragment migrated as a single band with decreased mobility compared to the unmodified fragment (FIG. 6A, lanes 4 and 1).

Figure 6B:
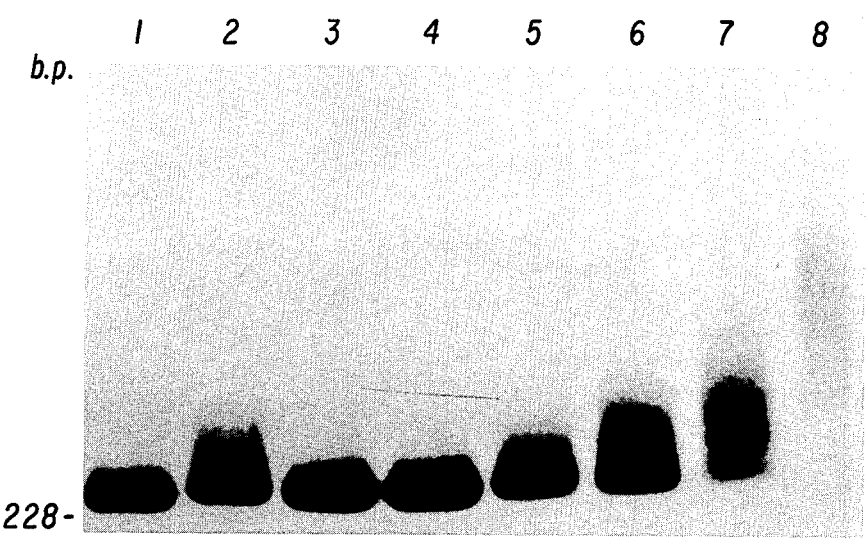

Higher reaction temperatures (37° C. and 45° C.) resulted in a progressive diffusion of the banding pattern (FIG. 6A, lanes 5 and 6). Following reaction with carbodiimide at 30° C. and 37° C. a 228 base pair blunt end SmaI fragment isolated from primer extended T9 (FIG. 4) did not produce a mobility shift (FIG. 6B, lanes 5 and 6). Higher temperatures (45° C. and 55° C.) caused changes in banding patterns similar to those described above (FIG. 6B, lanes 7 and 8).

Reactivity of Carbodiimide with a 6 Base Internal Unpaired Region

Figure 7:
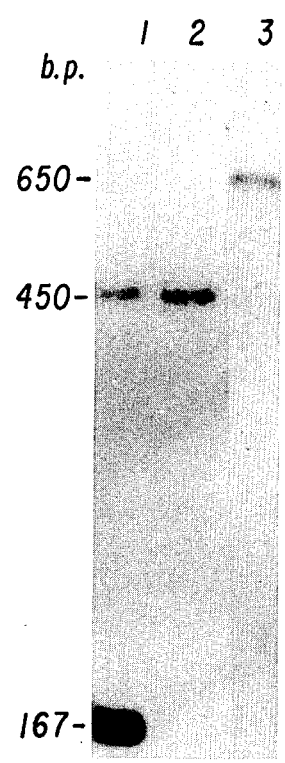

To test the reactivity of carbodiimide with internal DNA mismatches heteroduplexes were formed between a fragment of the H-ras oncogene and its homologue (FIG. 5). The six base unpaired region which occurs in the heteroduplexed DNA molecules causes a large decrease in migration of the fragment through a polyacrylamide gel. This fact allows one to quantitatively purify heteroduplexed fragments away from any reannealed, perfectly paired fragments. For a 167 base pair Sma I fragment isolated from heteroduplex A (FIG. 5), the size base unpaired region causes a decrease in mobility such that the fragment migrates in a 12% gel with an apparent length of 650 base pairs (FIG. 7, lane 3).

Figure 8:
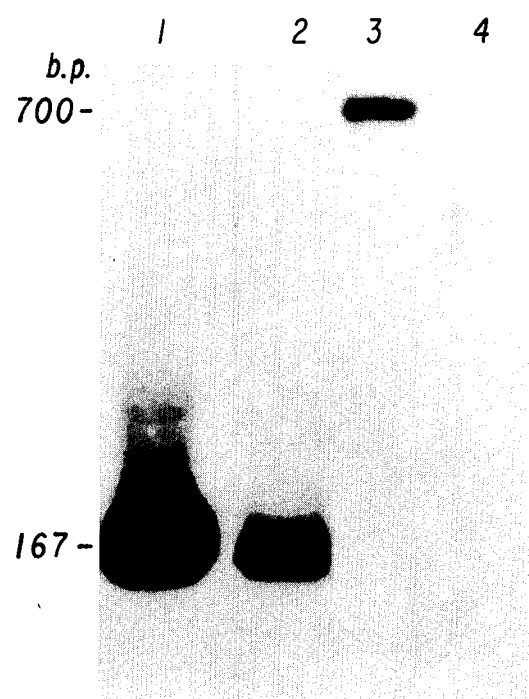

DNA fragments were electroeluted from a gel slice and purified as described in Materials and Methods prior to carbodiimide modification. The 6 base unpaired region in the 167 base pair SmaI fragment from heteroduplex A has five potential sites of carbodiimide modification within the sequence GGGGCT. A change in gel mobility after reaction with carbodiimide would correlate with the predicted modification of these unpaired bases. After reaction with carbodiimide at 30° C., the heteroduplex migrated through the 12% polyacrylamide gel more rapidly as evidenced by the appearance of several diffuse new bands (FIG. 8, lane 4). Under the same conditions or carbodiimide modification, the 167 base pair homoduplex showed no electrophoretic mobility change (FIG. 8, lane 2).

Figure 9:
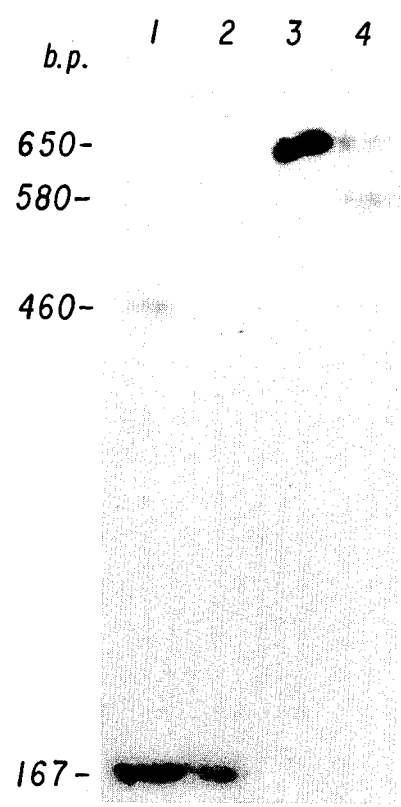

The Sma I fragment isolated from heteroduplex C (FIG. 5) contains a six base unpaired region with the complementary sequence (CCCCGA). This heteroduplex also migrated with fragments of 650 base pairs in length, but contains only one potential site of modification by carbodiimide. Following reaction iith carbodiimide at 30° C., the fragment showed a single, distinct band of greater mobility with an apparent length of 580 base pairs (FIG. 9, lane 4).

Reaction of Carbodiimide with Single Base Mismatches

Mobility shifts caused by modifications of small unpaired regions of DNA suggested the application of the tecnnique to a DNA fragment containing a single base mismatch. A 228 base pair Sma I fragment was ioolated from heteroduplex B (FIG. 5). Forty-five base pairs separate two single base mismatches in this fragment. The fragment was reacted with carbodiimide at various temperatures. After reaction with carbodiimide, cleavage at a unique Sau IIIAI site between the mismatches generated a 91 base pair fragment containing a T-C mismatch and a 137 base pair fragment containing a T-G mismatch.

Figure 10A:
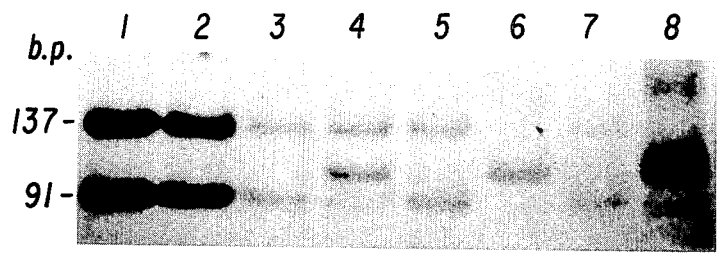

The DNA fragments were electrophoresed through a 15% polyacrylamide gel (FIG. 10A). Fragments containing a single base mismatch had the same mobility as the corresponding homoduplex fragment, therefore, a single base mismatch is not sufficient for DNA separation.

After carbodiimide reaction at 30° C., the 91 base pair heteroduplex containing a T-C mismatch showed a decrease in mobility compared to the 91 base pair homoduplex (FIG. 10A, lanes 4 and 3). The 137 base pair heteroduplex (with a T-G mismatch) showed no difference in mobility at 30° C. However, following carbodiimide reaction at 37° C., the 137 base pair heteroduplex showed a decreased mobility compared to the identically treated homoduplex (FIG. 10A, lanes 6 and 5). Under these conditions the 91 base pair heteroduplex showed the same decreased mobility as seen following reaction at 30° C. Reaction of DNA with carbodiimide at 45° C. resulted in decreased mobility for both homoduplex and heteroduplex molecules (FIG. 10A, lanes 7 and 8).

Figure 10B:
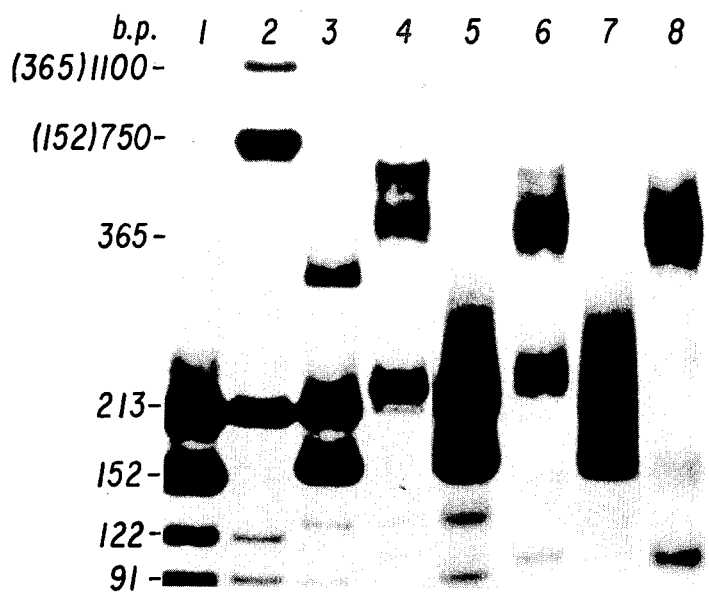

A 361 base pair Pst I fragment from heteroduplex A was reacted with carbodiimide and only then cleaved with Sma I and Sau IIIAI. In this experiment the Sau IIIAI did not cut to completion providing the opportunity to compare the relative mobility shifts caused by reaction with carbodiimide at single base mismatches, unpaired restriction fragment ends and internal unpaired regions (FIG. 10B). Following carbodiimide reaction at 30° C., the 91 base pair Sma I/Sau IIIAI blunt end heteroduplex, which contains a T-C mismatch, showed a 4% reduction in mobility compared to unmodified heteroduplex (FIG. 10B, lanes 4 and 2). Under the same conditions the 122 base pair Sau IIIAI/Pst I homoduplex showed a 3% reduction in mobility as compared to the unmodified species (FIG. 10B, lanes 3 and 1). The 122 base pair heteroduplex, which contains a T-G mismatch exhibited two stages of mobility shift. The first, a 3% reduction, was due to reaction of carbodiimide at 30° C. at the Pst I end compared to unmodified heteroduplex (FIG. 10B, lanes 4 and 2). The second, was due to reaction of the T-G mismatch at 37° C. and resulted in an additional 9% reduction in mobility compared to heteroduplex modified at 30° C. (FIG. 10B, lanes 6 and 4). The 213 base pair Sma I/Pst I heteroduplex exhibited a similar two stage mobility shift. The first, at 30° C., was due to reactivity of a Pst I end and the T-C mismatch (FIG. 10B, lanes 2 and 4). The second, at 37° C., was due to reactivity of the T-G mismatch (FIG. 10B, lanes 4 and 6). DNA fragments containing the internal unpaired region (152 base pair Pst I/Sma I fragmnnt and 365 base pair Pst I fragment) both moved with markedly decreased mobility as compared to their corresponding homoduplex DNA segments (FIG. 10B, lanes 2 and 1). Reaction with carbodiimide created heteroduplex molecules with somewhat increased mobility in comparison with the unreacted heteroduplex molecules (FIG. 10B, lanes 4, 6, and 8 compared to lane 2).

This example has demonstrated the ability of carbodiimide to bind to single stranded regions of duplex DNA (to serve) the basis for development of a system for distinguishing DNA fragments based on sequence differences. Mismatches and unpaired regions in otherwise perfectly paired DNA fragments, were generated by heteroduplex formation between the denatured strands of homologous fragments containing base substitutions and additions or deletions. Altered mobility on a high percentage polyacrylamide gel was used to detect the reactivity of these heteroduplex molecules with carbodiimide. Single base mismatches and unpaired regions reacted with carbodiimide at 30° C. and 37° C., while perfectly paired DNA remained unreactive. The relative instability of the T-C mismatch allowed it to be modified at a lower temperature than a T-G mismatch (Crick, F. H. C., *J. Mol. Biol.* 19:548:555 (1966)). Higher temperatures may result in breathing along the molecule and at the fragment ends (Lu, P. et al. *J. Biomol. Struct and Dynamics* 1:509–521(1983)) allowing carbodiimide access to internal bases.

Three substrates caused a reduction in electrophoretic mobility following carbodiimide modification. The T and G residues of the Pst I staggered ends caused a 3% reduction; the T of a T-C mismatch in an otherwise duplex fragment cause a 4% reduction and modification of both the T and G of a T-G mismatch caused a 9% reduction in gel mobility. Although not wishing to be bound to a particular theory these results are consistent with the following explanation: In gels of 12–15% acrylamide, the average "pore" is a small multiple of the cross-sectional area of DNA (Fisher SG and Lermen, L. S. supra 1983)). With the DNA threading end on through the matrix, one or several carbodiimide molecules bound to the single stranded Pst I ends added only a small increment to the cross-sectional area and resulted in a small reduction in gel mobility. Carbodiimide bound to the T of a T-C mismatch would be expected to lie outside the helix adding significantly to the cross-sectional area and resulting in a greater reduction in gel mobility. Reaction of carbodiimide with a G-T mismatch resulted in an adduct with two molecules of carbodiimide bound, both lying outside the helix; further reducing gel mobility because of the still greater local cross-sectional area.

The 167 base pair Sma I fragment isolated from heteroduplex A (FIG. 5), demonstrated a completely different pattern of change in gel mobility following carbodiimide modification. The single strands from which the heteroduplex were formed differ by only six contiguous base pairs: yet these molecules migrated 55% slower then either perfectly paired parent homoduplex (FIG. 7). It is unlikely that such a large reduction in electrophoretic mobility was caused by just six unpaired bases in the duplex.

An alternative explanation is that the six unpaired bases cause a bend in the structure of the DNA molecule, greatly reducing the electrophoretic mobility. Carbodiimide modification partially relieves the distortion and results in a faster migrating molecule.

The method described herein is useful in elucidating the genetic basis of both phenotypic variation and heritable human disease. Since many single base changes of clinical significance do not necessarily occur at a known restriction enzyme site (Kidd, U. J. et al. *Nature* 304:230–34 (1983)), analysis of changes in digestion patterns is of limited utility. Further while current oligonucleotide probe technology is able to detect any DNA base change, it is costly, technically difficult, and requires prior sequence information. Carbodiimide modification provides a useful alternative to current methods of mutant detection. Also by "tagging" mismatches with carbodiimide, molecules which include critical sequence differences can be purified as disclosed above.

What is claimed is:

1. A method for detecting guanine and thymine bases which are unpaired according to the Watson-Crick base pairing scheme in a double stranded polynucleotide molecule, each unpaired guanine or thymine base being immediately preceded by at least one base which is paired, and immediately followed by at least one base which is paired, said preceding and following paired bases being on the same polynucleotide sequence as the unpaired guanine or thymine base comprising:

(a) reacting the double stranded polynucleotide molecule with a reagent capable of altering the electrophoretic mobility of a double stranded polynucleotide molecule by derivatizing unpaired guanine and thymine bases in the double stranded polynucleotide molecule, wherein the double strandned polynucleotide molecule is not a covalently closed circular DNA;

(b) observing the electrophoretic mobility of the double stranded polynucleotide molecule which has been reacted with the reagent; and (c) determining the presence or absence of an alteration in the electrophoretic mobility;

whereby the presence or absence of unpaired guanine and thymine bases in the double stranded polynucleotide molecule is detected.

2. A method for detecting guanine and thymine bases which are unpaired according to the Watson-Crick base pairing scheme in a double stranded polynucleotide molecule, wherein each unpaired guanine or thymine base being immediately preceded by at least one base which is paired and immediately followed by at least one base which is paired, said preceding and following paired bases being on the same polynucleotide sequence as the unpaired guanine or thymine base comprising:

(a) hybridizing a first single stranded polynucleotide sequence with a second single stranded polynucleotide sequence to form a double stranded polynucleotide molecule;

(b) reacting the double stranded polynucleotide molecule with a reagent capable of altering the electrophoretic mobility of a double stranded polynucleotide molecule by derivatizing unpaired guanine and thymine bases in the double stranded polynucleotide molecule;

(c) observing the state of electrophoretic mobility the double stranded polynucleotide molecule which has been reacted with the reagent;

(d) determining the presence or absence of an alteration in the state of the property, wherein the presence or absence of unpaired guanine and thymine bases in the double stranded polynucletide molecule is detected.

3. The method of claim 2 wherein the unpaired guanine and thymine bases are mispaired according to the Watson-Crick base pairing scheme.

4. The method of claim 2 wherein each unpaired guanine or thymine base is immediately preceded by a first plurality of bases all of which are paired and immediately followed by a second plurality of bases all of which are paired, said preceding and following pluralities of paired bases being on the same polynucleotide sequence as the unpaired guanine or thymine base.

5. The method of claim 4 wherein the first plurality is at least 40 and the second plurality is at least 40.

6. The method of claim 2 wherein the reagent is a carbodiimide.

7. The method of claim 6 wherein:

(i) step (b) comprises reacting the double stranded polynucleotide molecule with about 0.1M carbodiimide at about pH 8.5, for about 4 hours at a temperature between about 25° C. and about 40° C.; and (ii) the first sequence and the second sequence are DNA.

8. The method of claim 7 wherein the carbodiimide is 1-cyclohexyl-3-(2-morpholino-ethyl) carbodiimide.

9. The method of claim 2 wherein the first sequence and the second sequence are DNA.

10. A method for purifying double stranded polynucleotide molecules that are base paired throughout the entire molecules according to the Watson-Crick scheme comprising:

(a) hybridizing a mixture of molecules comprising single stranded polynucleotide sequences to form double stranded polynucleotide molecules;

(b) reacting the double stranded polynucleotide molecules with a reagent capable of altering the electrophoretic mobility of a double stranded polynucleotide molecule by derivatizing unpaired guanine and thymine bases in the double stranded polynucleotide molecule, each unpaired guanine or thymine base being immediately preceded by at least one base which is paired and immediately followed by at least one base which is paired, said preceding and following paired bases being on the same polynucleotide sequence as the unpaired guanine or thymine base;

(c) selectively separating underivatized polynucleotide molecules from derivatized polynucleotide molecules according to the electrophoretic mobility, whereby double stranded polynucleotide molecules that are based paired throughout the entire molecules are purified.

11. The method of claim 10 wherein the unpaired guanine and thymine bases are mispaired according to the Watson-Crick base pairing scheme.

12. The method of claim 10 wherein each unpaired guanine or thymine base is immediately preceded by a plurality of bases all of which are paired and immediately followed by a second plurality of bases all of which are paired, said preceding and following pluralities of paired bases being on the same polynucleotide sequence as the unpaired guanine or thymine base.

13. The method of claim 12 wherein the first plurality is at least 40 and the second plurality is at least 40.

14. The method of claim 10 wherein step (b) comprises reacting the double stranded polynucleotide molecules with about 0.1M carbodiimide at about pH 8.5, for about 4 hours.

15. The method of claim 10 wherein step (c) comprises molecularly cloning and biologically selecting the underivatized polynucleotide molecules in an environment which is incapable of replicating derivatized DNA.

16. The method of claim 15 wherein the derivatized DNA is carbodiimide-derivatized DNA.

17. The method of claim 16 wherein the environment incapable of replicating derivatized DNA is the cellular environment of replicating derivatized DNA is the cellular environment of a UVRA, RecA host.

18. The method of claim 10 wherein:

(A) step (b) comprises reacting the double stranded polynucleotide molecules with about 0.1M carbodiimide at about pH 8.5, for about 4 hours;

(B) step (c) comprises:

(i) electrophoresing the double stranded polynucleotide molecules which have been reacted with carbodiimide in a first dimension;

(ii) removing the carbodiimide which has become bound to double stranded polynucleotide molecules by treating the double stranded polynucleotides with alkali;

(iii) further electrophoresing the double stranded polynucleotide molecules in a second dimension; and (iv) identifying and obtaining the double stranded polynucleotide molecules which have electrophoretic mobilities in step (iii) different from their electrophoretic mobilities in step (i).

19. The method according to claim 10 wherein the mixture of molecules comprising single stranded polynucleotide sequences is obtained from two individuals having a common ancestor.

20. The method of claim 19 wherein the number of generations separating the two individuals is six.

21. The method of claim 19 wherein the two individuals and their common ancestors are predisposed to, have or had a genetic disease.

22. The method of claim 19 wherein the genetic disease is selected from the group consisting of breast cancer, colon cancer, and cystic fibrosis.

23. A method for detecting the presence or absence of bases which are mispaired according to the Watson-Crick base pairing scheme in a double stranded polynucleotide molecule, and which mispaired bases are immediately preceded by at least one base which is paired, and immediately followed by at least one base which is paired, said preceding and following paired bases being on the same polynucleotide sequence as the unpaired base, comprising:
  (a) reacting the double stranded polynucleotide molecule with a reagent capable of altering the electrophoretic mobility of a double stranded polynucleotide molecule by derivatizing at least one mispaired baes in the double stranded polynucleotide molecule, wherein the double stranded polynucleotide molecule is not a covalently closed circular DNA;
  (b) observing the electrophoretic mobility of the double stranded polynucleotide molecule which has been reacted with the reagent;
  (c) determining the presence or absence of an alteration in the electrophoretic mobility,
whereby the presence or absence of at least one mispaired base in the double stranded polynucleotide molecule is detected.

24. A method for detecting the presence or absence of bases which are mispaired according to the Watson-Crick base pairing scheme in a double stranded polynucleotide molecule, and which mispaired bases are immediately preceded by at least one base which is paired, and immediately followed by at least one base which is paired, said preceding and following paired bases being on the same polynucleotide sequence as the unpaired base, comprising:
  (a) hybridizing a first single stranded polynucleotide sequence with a second single stranded poyynucleotide sequence to form a double stranded polynucleotide molecule;
  (b) reacting the double stranded polynucleotide molecule with a reagent capable of altering the electrophoretic mobility of a double stranded polynucleotide molecule by derivatizing at least one mispaired base in the double stranded polynucleotide molecule;
  (c) observing the electrophoretic mobility of the double stranded polynucleotide molecule which has been reacted with the reagent;
  (d) determining the presence or absence of an alteration in the electrophoretic mobility,
whereby the presence or absence of at least one mispaired base in the double stranded polynucleotide molecule is detected.

25. The method of claim 24 wherein the reagent is a carbodiimide.

26. The method of claim 25 wherein:
  (i) step (b) comprises reacting the double stranded polynucleotide molecule with about 0.1M carbodiimide at about pH 8.5, for about 4 hours at a temperature between about 25° C. and about 40° C.; and
  (ii) the first sequence and the second sequence are DNA.

27. A method for purifying double stranded polynucleotide molecules that are base paired throughout the entire molecules according to the Watson-Crick scheme comprising:
  (a) hybridizing a mixture of molecules comprising single stranded polynucleotide sequences to form double stranded polynucleotide molecules;
  (b) reacting the double standed polynucleotide molecules with a reagent capable of altering the elelctrophoretic mobility of a double stranded polynucleotide molecule by derivatizing at least one mispaired base in the double stranded polynucleotide molecule, wherein each mispaired base is immediately preceded by at least one base which is paired and immediately followed by at least one base which is paired, said preceding and following paired bases being on the same polynucleotide sequence as said mispaired base;
  (c) selectively separating underivatized polynucleotide molecules from derivatized polynucleotide molecules according to the electrophoretic mobility,
whereby double stranded polynucleotide molecules that are based paired throughout the entire molecules are purified.

28. The method of claim 27 wherein each mispaired base is immediately preceded by a first plurality of bases all of which are paired and immediately followed by a second plurality of bases all of which are paired, said preceding and following pluralities of paired bases being on the same polynucleotide sequence as said mispaired base.

29. The method of claim 28 wherein the first plurality is at least 40 and the second plurality is at least 40.

30. The method of claim 27 wherein step (b) comprises reacting the double stranded polynucleotide molecules with about 0.1M carbodiimide at about pH 8.5, for about 4 hours.

31. The method of claim 27 wherein step (c) comprises molecularly cloning and biologically selecting the underivatized polynucleotide molecules in an environment which is incapable of replicating derivatized DNA.

32. The method of claim 31 wherein the derivatized DNA is carbodiimide-derivatized DNA.

33. The method of claim 32 wherein the environment incapable of replicating derivatized DNA is the cellular environment of a UVRA, RecA host.

34. The method of claim 27 wherein:
  (A) step (b) comprises reacting the double stranded polynucleotide molecules with about 0.1M carbodiimide at about pH 8.5, for about 4 hours;
  (B) step (c) comprises:
  (i) electrophoresing the double stranded polynucleotide molecules which have been reacted with carbodiimide in a first dimension;
  (ii) removing the carbodiimide which has become bound to double stranded polynucleotide molecules by treating the double stranded polynucleotides with alkali;

(iii) further electrophoresing the double stranded polynucleotide molecules in a second dimension; and (iv) identifying and obtaining the double stranded polynucleotide molecules which have electrophoretic mobilities in step (iii) different from their electrophoretic mobilities in step (i).

35. The method according to claim 27 wherein the mixture of molecules comprising single stranded polynucleotide sequences is obtained from two individuals having a common ancestor.

36. The method of claim 35 wherein the number of generations separating the two individuals is six.

37. The method of claim 35 wherein the two individuals and their common ancestors are predisposed to, have or had a genetic disease.

38. The method of claim 35 wherein the genetic disease is selected from the group consisting of breast cancer, colon cancer, and cystic fibrosis.

* * * * *

UNITED STATES PATENT AND TRADEMARK OFFICE
CERTIFICATE OF CORRECTION

PATENT NO. : 4,794,075

DATED : December 27, 1988

INVENTOR(S) : Ford et al.

Page 1 of 2

It is certified that error appears in the above-identified patent and that said Letters Patent is hereby corrected as shown below:

Cover page, thirteenth line of the abstract, delete "located" and insert --locate--. Column 1, line 45 and column 14, line 11, delete "Fisher" and insert --Fischer-- at each occurrence. Column 2, line 21, delete "mixture" and insert --a mixture of--; line 35, delete "wil" and insert --will--. Column 3, line 9, delete "P9Rf" and insert --P9RF--; line 67, delete "ccar-" and insert --car---. Column 5, line 35, delete "eepresent" and insert --represent--; line 36, delete "mutation" and insert --mutations--. Column 6, line 54, delete "will" and insert --that will be--. Column 7, line 2, delete "in" and insert --from a--; line 30, delete "performed" and insert --is performed--; line 45, delete "has" and insert --has a--; line 49, delete "combination" and insert --combinations--; line 52, delete "AluI" and insert --of the AluI--. Column 8, line 19, delete "andone" and insert --and one--; line 47, delete "Thus the" and insert --Thus--. Column 9, line 36, delete "results" and insert --result--; line 37, delete "ern's" and insert --erns--. Column 10, line 29, delete "orientation" and insert --orientations--; line 57, delete "minutes (FIG. 5)." and insert --minutes.--; line 63, delete "acrllamide:Bis" and insert --acrylamide:Bis--. Column 11, line 10, delete "acetaee" and insert --acetate--; line 26, delete "codin" and insert --coding--. Column 12, line 14, delete "size" and insert --six--;

UNITED STATES PATENT AND TRADEMARK OFFICE
CERTIFICATE OF CORRECTION

PATENT NO. : 4,794,075

DATED : December 27, 1988

INVENTOR(S) : Ford et al.

It is certified that error appears in the above-identified patent and that said Letters Patent is hereby corrected as shown below:

column 12, line 38, delete "iith" and insert --with--; line 44, delete "modifications" and insert --modification--; line 47, delete "ioolated" and insert --isolated--. Column 13, line 40, delete "fragmnnt" and insert --fragment--. Claim 1, subsection (a), at column 15, line 2, delete "strandned" and insert --stranded--. Claim 17 at column 16, line 50, delete entire line "environment of replicating derivatized DNA is the"; line 51, delete "cellular".

Signed and Sealed this

Twelfth Day of September, 1989

Attest:

DONALD J. QUIGG

Attesting Officer

Commissioner of Patents and Trademarks